(12) United States Patent
Suzuki

(10) Patent No.: US 9,216,948 B2
(45) Date of Patent: Dec. 22, 2015

(54) METHOD FOR PRODUCING COPOLYMER FOR SEMICONDUCTOR LITHOGRAPHY CONTAINING REDUCED AMOUNT OF METAL IMPURITIES, AND METHOD FOR PURIFYING POLYMERIZATION INITIATOR FOR PRODUCTION OF COPOLYMER

(75) Inventor: Youji Suzuki, Kisarazu (JP)

(73) Assignee: Maruzen Petrochemical Co., Ltd., Chuo-Ku (JP)

( * ) Notice: Subject to any disclaimer, the term of this patent is extended or adjusted under 35 U.S.C. 154(b) by 739 days.

(21) Appl. No.: 13/451,793

(22) Filed: Apr. 20, 2012

(65) Prior Publication Data

US 2012/0271020 A1    Oct. 25, 2012

(30) Foreign Application Priority Data

Apr. 21, 2011  (JP) ................. 2011-095415

(51) Int. Cl.
| | |
|---|---|
| C08F 220/20 | (2006.01) |
| C07C 245/04 | (2006.01) |
| C08F 222/20 | (2006.01) |
| C08F 20/12 | (2006.01) |
| C08F 20/02 | (2006.01) |
| C08F 20/64 | (2006.01) |
| C08F 16/26 | (2006.01) |
| C07C 245/00 | (2006.01) |
| C08F 20/06 | (2006.01) |
| C08F 16/10 | (2006.01) |
| C07B 63/00 | (2006.01) |
| C08F 20/26 | (2006.01) |
| C08F 16/04 | (2006.01) |

(52) U.S. Cl.
CPC ............ *C07C 245/04* (2013.01); *C08F 222/20* (2013.01); *C07B 63/00* (2013.01); *C07C 245/00* (2013.01); *C08F 16/04* (2013.01); *C08F 16/10* (2013.01); *C08F 16/26* (2013.01); *C08F 20/02* (2013.01); *C08F 20/06* (2013.01); *C08F 20/12* (2013.01); *C08F 20/26* (2013.01); *C08F 20/64* (2013.01); *C08F 220/20* (2013.01)

(58) Field of Classification Search
CPC ..... C07B 63/00; C07C 245/00; C08F 220/20; C08F 16/04; C08F 16/10; C08F 20/02; C08F 20/06; C08F 20/64; C08F 20/12; C08F 20/26; C08F 16/26
See application file for complete search history.

(56) References Cited

U.S. PATENT DOCUMENTS

| | | | |
|---|---|---|---|
| 4,568,466 A | 2/1986 | Salem et al. | |
| 7,015,291 B2 | 3/2006 | Watanabe et al. | |
| 7,655,743 B2 | 2/2010 | Watanabe et al. | |
| 7,662,897 B2 | 2/2010 | Watanabe et al. | |
| 7,816,471 B2 | 10/2010 | Watanabe et al. | |
| 2006/0116494 A1 | 6/2006 | Watanabe et al. | |
| 2008/0114139 A1 | 5/2008 | Yamagishi et al. | |
| 2010/0038831 A1 | 2/2010 | Kawaguchi et al. | |
| 2010/0062371 A1* | 3/2010 | Oikawa et al. | 430/286.1 |
| 2010/0324245 A1 | 12/2010 | Yamagishi et al. | |

FOREIGN PATENT DOCUMENTS

| | | |
|---|---|---|
| JP | 60-187390 A1 | 9/1985 |
| JP | 60-220303 A1 | 11/1985 |
| JP | 07-074073 A1 | 3/1995 |
| JP | 09-143237 A1 | 6/1997 |
| JP | 11-512713 A1 | 11/1999 |
| JP | 2000-516133 A1 | 12/2000 |
| JP | 2001-201868 A1 | 7/2001 |
| JP | 2002-182402 A1 | 6/2002 |
| JP | 2002-226436 A1 | 8/2002 |
| JP | 2003-040925 A1 | 2/2003 |
| JP | 2003-342319 A1 | 12/2003 |
| JP | 2004-027396 A1 | 1/2004 |
| JP | 2006-037117 A1 | 2/2006 |
| JP | 2006-188575 A1 | 7/2006 |
| JP | 2008-038013 A1 | 2/2008 |
| JP | 2008-074909 A1 | 4/2008 |
| JP | 2008-088291 A1 | 4/2008 |
| JP | 2008074909 A * | 4/2008 |
| JP | 2008-111073 A1 | 5/2008 |
| JP | 2010-209338 A1 | 9/2010 |
| WO | 97/11929 A1 | 4/1997 |
| WO | 98/04348 A1 | 2/1998 |
| WO | 2005/105869 A1 | 11/2005 |
| WO | 2008/155928 A1 | 12/2008 |

OTHER PUBLICATIONS

Japanese Office Action (Application No. 2011-095415) dated Nov. 7, 2014.

* cited by examiner

*Primary Examiner* — Richard A Huhn

(74) *Attorney, Agent, or Firm* — Burr & Brown, PLLC

(57) ABSTRACT

A method for producing a copolymer for semiconductor lithography containing less metal impurities, and a method for purifying a polymerization initiator for production of the copolymer, are provided. The method for purifying a polymerization initiator to be used for production of a polymer includes a filtering step wherein a solution of a polymerization initiator dissolved in an organic solvent is allowed to pass through a filter having a nominal pore size of not more than 1.0 μm, to reduce the sodium content of the polymerization initiator solution to not more than 300 ppb with respect to the weight of the polymerization initiator. Further, the method for producing a copolymer for semiconductor lithography includes a polymerization step wherein the polymer for semiconductor lithography is synthesized by a radical polymerization reaction in the presence of a polymerization initiator purified by the above purification method.

10 Claims, No Drawings

METHOD FOR PRODUCING COPOLYMER FOR SEMICONDUCTOR LITHOGRAPHY CONTAINING REDUCED AMOUNT OF METAL IMPURITIES, AND METHOD FOR PURIFYING POLYMERIZATION INITIATOR FOR PRODUCTION OF COPOLYMER

BACKGROUND OF THE INVENTION

1. Field of the Invention

The present invention relates to a method for producing a copolymer for lithography to be used for production of a semiconductor, and a method for purifying a polymerization initiator for production of the copolymer. More particularly, the present invention relates to a method for producing a copolymer for semiconductor lithography with a reduced amount of metal impurities, which is suitable for obtaining a semiconductor having excellent electrical properties, and a purification method for obtaining a polymerization initiator with a reduced amount of metal impurities, for production of the copolymer.

2. Description of Related Art

In lithography used for production of a semiconductor, formation of a finer pattern is increasingly demanded due to increase in the integration density, and, at present, lithography techniques with KrF excimer laser light (with a wave length of 248 nm) or ArF excimer laser light (with a wavelength of 193 nm) are used for mass production. Further, research and development are in progress also for lithography techniques using F2 excimer laser light, which has a shorter wavelength (a wavelength of 157 nm), EUV (extreme ultraviolet) and X-ray, which have still shorter wavelengths than those excimer lasers, and the electron beam.

As miniaturization of the patterns proceeds, reduction of the amount of impurities contained in copolymers to be used for semiconductor lithography has been increasingly demanded. Since, in particular, metal impurities adversely affect production of semiconductors in various ways, they need to be removed as much as possible. For example, in cases where metal impurities such as sodium and iron are contained in a copolymer for a chemical amplification resist, the metal components capture an acidic substance generated from an acid generator during exposure, and a copolymer as a base component is therefore not sufficiently dissolved, so that a desired pattern cannot be formed. Further, in cases where metal impurities contained in a copolymer for semiconductor lithography, which is not restricted to a resist copolymer and may be a topcoat copolymer, antireflection coating copolymer or the like, finally remain on the surface of a semiconductor substrate, electrical properties of the semiconductor are impaired, leading to decrease in the yield of the product.

Reported examples of the method for removing metal impurities from copolymers for semiconductor lithography include a method wherein a copolymer is subjected to extraction with an organic solvent and water to distribute the copolymer into the organic layer and the metals into the aqueous layer, followed by removal of the aqueous layer (Patent Document 1) and a method wherein, to a solution of an alicyclic hydrocarbon polymer in an organic solvent, a poor solvent for the polymer and an acid are added to cause coagulation of the polymer, and the coagulated polymer, water-insoluble organic solvent, acid and water are mixed together to extract metals (Patent Document 2). Further reported examples of the method include a method wherein a novolak resin solution is allowed to pass through a cation-exchange resin and anion-exchange resin washed with deionized water and a mineral acid solution (Patent Document 3), a method wherein a dispersion prepared by dispersing a polymer in a dispersion medium is filtered through a filter such as a filter cloth preliminarily washed with an acidic aqueous solution, to obtain wet polymer powder with a reduced metal content (Patent Document 4) and a method wherein a polymer solution is allowed to pass through an absorbent such as a clay intercalation compound, active carbon or silica gel, to remove metals (Patent Document 5). Other reported examples include a method wherein, to a resist polymer solution, a water-soluble compound capable of forming a complex is added at an equivalent larger than that of metal purities in the polymer to complete the reaction, followed by washing the reaction product with pure water (Patent Document 6). However, operations in these methods are laborious, and it has been difficult to apply the methods to commercial-scale production of copolymers.

On the other hand, as an alternative to the methods in which metals are removed after production of a copolymer, there is a method wherein a raw material with a reduced metal content is used to reduce metals contained in a copolymer. Reported examples of such a method include a method wherein monomers as a raw material of a photoresist polymer is obtained by thin film distillation, which monomers contain each of Na, Mg, K, Ca, Mn, Fe and Cu with a content of not more than 50 ppb (Patent Document 7), a method wherein a (meth)acrylic acid ester having a cyclic skeleton such as an adamantane skeleton or lactone skeleton is subjected to molecular distillation or adsorption treatment with a chelate resin, to obtain a (meth)acrylic acid ester having a cyclic skeleton, whose metal content is not more than 500 ppb (Patent Document 8) and a method wherein monomers are washed with ultrapure water (Patent Document 9).

By the way, a polymerization initiator is also an important raw material. The molecular weight of a copolymer for semiconductor lithography is often relatively small as a macromolecule. Therefore, the amount of a polymerization initiator to be used is relatively large, and is often as large as several mol % to ten and several mol % with respect to the total amount of the raw material monomers. In particular, an azo polymerization initiator sometimes contains metals at a high concentration, which metals are derived by the production process of the polymerization initiator. Therefore, there is a concern that the metals largely affect the metal content of the copolymer produced using the polymerization initiator. As a method for reducing the metal content of a polymerization initiator, there is a method (Patent Document 10) wherein water is added to a solution of an azo polymerization initiator in a water-insoluble solvent, to extract metals into the aqueous layer, followed by removing the metals. In this case, it has been reported that the sodium content is reduced from 3300 ppb to not more than 500 ppb with respect to the polymerization initiator by one time of the extraction operation. However, there are problems in that, for example, this method requires additional steps and produces additional waste fluid.

PRIOR ART DOCUMENTS

Patent Documents

[Patent Document 1] JP 2006-037117 A
[Patent Document 2] JP 2003-342319 A
[Patent Document 3] JP 09-143237 A
[Patent Document 4] JP 2008-038013 A
[Patent Document 5] JP 07-074073 A
[Patent Document 6] JP 2002-182402 A
[Patent Document 7] JP 2001-201868 A

[Patent Document 8] JP 2002-226436 A
[Patent Document 9] JP 2006-188575 A
[Patent Document 10] JP 2008-074909 A

SUMMARY OF THE INVENTION

Problems to be Solved by the Invention

The present invention aims to provide a method wherein metal impurities in a polymerization initiator to be used for production of a copolymer for semiconductor lithography are efficiently removed by a simple and low-cost process, and the polymerization initiator with a reduced content of metal impurities is used to produce a copolymer for semiconductor lithography in which the content of metal impurities is extremely low.

Means for Solving the Problems

The present inventors intensively studied to solve the above problems, and discovered that, by dissolving a polymerization initiator to be used in production of a copolymer for semiconductor lithography in a solvent and allowing the resulting solution to pass through a filter having a specific pore size, the metal content of the polymerization initiator can be very simply reduced, and the polymerization initiator can be used to produce a copolymer for semiconductor lithography containing a reduced amount of metal impurities, thereby completing the present invention.

That is, according to an embodiment of the present invention,
a method for purifying a polymerization initiator to be used in production of a polymer,
the method comprising a filtering step wherein a solution of a polymerization initiator dissolved in an organic solvent is allowed to pass through a filter having a nominal pore size of not more than 1.0 µm, to reduce the sodium content of the polymerization initiator solution to not more than 300 ppb with respect to the weight of the polymerization initiator is provided.

That is, according to an embodiment of the present invention,
a method for producing a polymer for semiconductor lithography, the polymer comprising at least one type of repeating units selected from the group consisting of: a repeating unit having a hydroxy group or carboxy group (A); a repeating unit having a structure wherein a hydroxy group or carboxy group is protected with a group that suppresses dissolution into an alkaline developer and is dissociable by the action of an acid (B); a repeating unit having a lactone structure (C); and a repeating unit having a cyclic ether structure (D);
the method comprising a polymerization step wherein the polymer for semiconductor lithography is synthesized in the presence of a polymerization initiator purified by the above-described purification method, by a radical polymerization reaction is provided.

That is, according to an embodiment of the present invention,
a method for producing a polymer for semiconductor lithography, the polymer comprising at least one type of repeating units selected from the group consisting of: a repeating unit having a hydroxy group or carboxy group (A); a repeating unit having a structure wherein a hydroxy group or carboxy group is protected with a group that suppresses dissolution into an alkaline developer and is dissociable by the action of an acid (B); a repeating unit having a lactone structure (C); and a repeating unit having a cyclic ether structure (D);
the method comprising a polymerization step wherein the polymer for semiconductor lithography is synthesized in the presence of a polymerization initiator by a radical polymerization reaction, which polymerization step uses a dropping polymerization method using a polymerization reactor at least comprising:
a storage tank for a solution comprising the polymerization initiator;
a polymerization reaction vessel; and
a filter placed in a channel connected from the storage tank to the polymerization reaction vessel, the filter having a nominal pore size of not more than 1.0 µm; is provided.

Effect of the Invention

According to the present invention, metal impurities in a polymerization initiator can be removed even with a filter having neither ion-exchange capacity nor zeta potential, as long as the filter has a pore size smaller than a specific size. Further, according to the present invention, a copolymer for semiconductor lithography containing a reduced amount of metal impurities can be produced without requiring major modification of the production apparatus, or laborious steps.

DETAILED DESCRIPTION OF THE INVENTION

Embodiments of the present invention are described below, but the present invention is not restricted to the embodiments below, and it should be understood that these embodiments are included within the scope of the present invention even in cases where they are, for example, appropriately modified or improved without departing from the spirit of the present invention based on the normal knowledge of those skilled in the art.

Method for Purifying Polymerization Initiator

The method according to the present invention for purifying a polymerization initiator to be used for production of a polymer comprises a filtering step wherein metal impurities are removed from the polymerization initiator. The filtering step is described in detail below.

Filtering step (Step of filtering a polymerization initiator)

The filtering step of the present invention is a step wherein metal impurities in a polymerization initiator to be used for production of a copolymer for semiconductor lithography are removed. Preferably, in filtering step, various types of metal impurities can be removed, and examples of the metal impurities include sodium, iron, potassium, calcium, aluminum, magnesium, lead and barium. Especially preferably, sodium can be removed in the step.

As the polymerization initiator to be used for production of a copolymer for semiconductor lithography, a known radical polymerization initiator may be used. Preferred examples of the polymerization initiator include radical polymerization initiators such as azo compounds and peroxides. Specific examples of azo compound-based polymerization initiators include 2,2'-azobisisobutyronitrile, 2,2'-azobis(2-methylbutyronitrile), dimethyl 2,2'-azobis(2-methylpropionate), 1,1'-azobis(cyclohexane-1-carbonitrile) and 4,4'-azobis(4-cyanovaleric acid). Specific examples of peroxide-based polymerization initiators include decanoyl peroxide, lauroyl peroxide, benzoyl peroxide, bis(3,5,5-trimethylhexanoyl) peroxide, succinic acid peroxide, tert-butylperoxy-2-ethylhexanoate, tert-butylperoxy pivalate and 1,1,3,3-tetramethylbutylperoxy-2-ethylhexanoate. These may be used either alone or as a mixture. An azo compound-based polymerization initiator is preferred since it is excellent in safety in handling. Further, since some products of azo compound-based polymerization initiators contain large amounts of metal components derived by their production methods, the effect of reduction of metals by the present invention may be large, which is preferred.

The organic solvent for dissolving the polymerization initiator is not restricted as long as the solvent dissolves the polymerization initiator. Specific examples of the organic solvent include ketones such as acetone, methyl ethyl ketone, methyl isobutyl ketone, methyl isoamyl ketone, methyl amyl ketone and cyclohexanone; alcohols such as methanol, ethanol and isopropanol; ether alcohols such as ethylene glycol monomethyl ether, ethylene glycol monoethyl ether, propylene glycol monomethyl ether and propylene glycol monoethyl ether; ether esters such as ethylene glycol monomethyl ether acetate, ethylene glycol monoethyl ether acetate, propylene glycol monomethyl ether acetate and propylene glycol monoethyl ether acetate; esters such as methyl acetate, ethyl acetate, propyl acetate, isopropyl acetate, butyl acetate, methyl propionate, methyl lactate and ethyl lactate; ethers such as tetrahydrofuran, 1,4-dioxane and ethylene glycol dimethyl ether; aromatic hydrocarbons such as toluene and xylene; N,N-dimethylformamide; and acetonitrile. These may be used either alone or as a mixture. Further, water may be added to an extent at which the water can be dissolved in the organic solvent and the polymerization initiator.

As the filter to be used in the filtering step of the present invention for removal of metals from the polymerization initiator, ones which are commercially available for liquid filtration may be normally used. The filter which may be used is preferably in the form of, for example, a membrane filter; hollow fiber membrane filter; pleated membrane filter; or a filter filled with a non-woven fabric, cellulose or diatomaceous earth. The filter material of the membrane filter, hollow fiber membrane filter and pleated membrane filter is preferably, for example, polyolefin such as polyethylene, very high density polyethylene or polypropylene; fluorocarbon polymer such as PTFE; or nylon. Further, the filters may contain an ion exchanger such as a cation-exchange resin, and/or a cation-controlling agent that gives a zeta-potential to the solution to be filtered, or the like.

The nominal pore size of the above filter is not more than 1.0 μm, preferably not more than 0.5 μm, more preferably not more than 0.03 μm. The lower limit of the nominal pore size of the filter is not restricted, and usually 0.01 μm. The nominal pore size herein means a nominal pore size indicating a separation performance of a filter, which is determined by a test method determined by the manufacturer of the filter, such as a bubble point test, mercury intrusion method or standard particle capture test. In cases where a commercially available product is used, the nominal pore size is the value described in the catalogue data provided by the manufacturer. By setting the nominal pore size to not more than 1.0 μm, the metal content of the polymerization initiator solution can be reduced to not more than 300 ppb by once passing through the filter, and the metal content of the copolymer produced using the polymerization initiator solution can also be reduced. In the present invention, the filtering step may be carried out 2 or more times in order to further reduce the metal content of the polymerization initiator.

Without wishing to be bound by theory, it is assumed that the mechanism of removal of metal impurities is as follows. However, needless to say, the present invention should not be restricted by the following explanation. Since metal components are in the ionized state in an aqueous solution and their diameters are extremely small, they can never be removed with a filter having a nominal pore size of about 0.01 to 1.0 μm. Therefore, the metal components are normally removed using a filter having ion-exchange capacity and/or a zeta potential. However, it is thought that, in cases where a polymerization initiator containing metal impurities are dissolved in an organic solvent, the metals cannot maintain their ionized state, and each metal particle may be in a state where several to ten and several, or more atoms are assembled to form a cluster. Thus, in the present invention, it was unexpectedly discovered that metal impurities in a polymerization initiator can be removed even with a filter having neither ion-exchange capacity nor zeta potential, as long as the filter has a nominal pore size which is not more than a specific size.

In cases where the temperature at the beginning of the purification of the polymerization initiator is too high, the polymerase initiator is degraded, which is not preferred, and, in cases where the temperature is too low, the solubility of the polymerization initiator in the solvent is small, leading to low efficiency. The temperature may be selected within the range of 0 to 40° C., preferably within the range of 5 to 30° C., especially preferably within the range of 10 to 25° C.

In the method according to the present invention for purifying a polymerization initiator, the polymerization initiator may be further processed through a purification step other than the filtering step, without restriction.

Method for Producing Polymer for Semiconductor Lithography

The method according to the present invention for producing a polymer for semiconductor lithography comprises a polymerization step wherein the polymer is synthesized in the presence of a polymerization initiator purified by the method according to the present invention for purifying a polymerization initiator, by a radical polymerization reaction. The production method according to the present invention may further include a purification step wherein the polymer obtained by the polymerization step is purified. The structure of the copolymer and each step are described below in detail.

In the method according to the present invention for producing a copolymer for semiconductor lithography, by using a polymerization initiator wherein the amount of metal impurities was reduced by the method according to the present invention for purifying a polymerization initiator, the amount of metal impurities contained in the polymer obtained by the polymerization step can be reduced.

In the method according to the present invention for producing a copolymer for semiconductor lithography, it is preferred to avoid washing treatment of the polymerization initiator with water. The washing treatment with water means a process in which water is added to a solution prepared by dissolving the polymerization initiator in a water-insoluble solvent, to extract metal impurities into the aqueous layer, thereby removing the metal impurities. Thus, the washing treatment with water requires additional steps and produces additional waste fluid.

Structure of Copolymer

The copolymer for semiconductor lithography produced by the present invention comprises at least one type of repeating units selected from the group consisting of: a repeating unit having a hydroxy group or carboxy group (A); a repeating unit having a structure wherein a hydroxy group or carboxy group is protected with a group that suppresses dissolution into an alkaline developer and is dissociable by the action of an acid (which may be hereinafter referred to as "acid-dissociable, dissolution inhibiting group") (B); a repeating unit having a lactone structure (C); and a repeating unit having a cyclic ether structure (D). Further, as required, the copolymer may comprise a repeating unit having a structure that suppresses dissolution into an alkaline developer and is stable against the action of an acid (which may be hereinafter referred to as "acid-stable, dissolution inhibiting structure") (E) and/or the like. These repeating units may be selected depending on the object of use of the thin film in semiconductor lithography.

For example, in cases where the copolymer is used for a chemical amplification positive resist film, the copolymer always comprises the repeating unit (B), and may comprise at least one type selected from the repeating units (A) and (C), and further, as required, the repeating unit (E). In cases where the copolymer is used for a negative resist film, the copolymer always comprises at least one type selected from the repeating units (A) and (D), and may comprise, as required, at least one type selected from the repeating units (C) and (E). In cases where the copolymer is used for an antireflection coating or an immersion topcoat, the copolymer always comprises at least one type selected from the repeating units (A) and (D), and may comprise, as required, at least one type selected from the repeating units (B), (C) and (E).

Repeating Unit (A)

The repeating unit (A) has a hydroxy group or carboxy group in its side chain, and enhances adhesion of the polymer to a substrate or bed layer, controls the solubility to a lithography solvent or alkaline developer, and/or gives a function to react with a curing agent to form a cross-linking structure.

As the structure of the repeating unit (A), the structures represented by Formulae (A1) to (A3) are especially preferred.

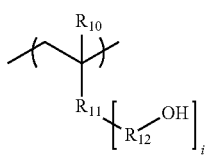

(A1)

In Formula (A1), $R_{10}$ represents a hydrogen atom, or $C_1$-$C_4$ hydrocarbon group which may be substituted with a fluorine atom(s), and specific examples of $R_{10}$ include a hydrogen atom; and $C_1$-$C_4$ alkyl which may be substituted with a fluorine atom(s), such as methyl, ethyl, n-propyl, i-propyl, n-butyl, i-butyl and trifluoromethyl. $R_{10}$ is preferably a hydrogen atom, methyl or trifluoromethyl. $R_{11}$ represents a substituted or unsubstituted aromatic hydrocarbon group. $R_{12}$ represents a single bond, or $C_1$-$C_4$ divalent hydrocarbon group which may be substituted with a fluorine atom(s), or carbonyl, and specific examples of $R_{12}$ include a single bond, and $C_1$-$C_4$ alkylene which may be substituted with a fluorine atom(s), such as methylene, 1,1-ethylene, 2,2-propylene, 1,1,1,3,3,3-hexafluoro-2,2-propylene and 1,1,1-trifluoro-2-trifluoromethyl-2,3-propylene. $R_{12}$ is preferably a single bond, 1,1,1,3,3,3-hexafluoro-2,2-propylene or 1,1,1-trifluoro-2-trifluoromethyl-2,3-propylene, and a single bond is especially preferred. i represents an integer of 1 or 2.

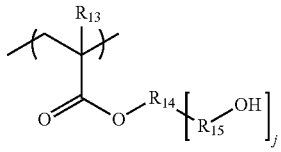

(A2)

In Formula (A2), $R_{13}$ represents a hydrogen atom, or $C_1$-$C_4$ hydrocarbon group which may be substituted with a fluorine atom(s), and specific examples of $R_{13}$ include a hydrogen atom; and $C_1$-$C_4$ alkyl which may be substituted with a fluorine atom(s), such as methyl, ethyl, n-propyl, i-propyl, n-butyl, i-butyl and trifluoromethyl. $R_{13}$ is preferably a hydrogen atom, methyl or trifluoromethyl. $R_{14}$ represents a $C_2$-$C_{14}$ divalent to tetravalent hydrocarbon group which may comprise a fluorine atom, oxygen atom and/or sulfur atom, and specific examples of $R_{14}$ include $C_2$-$C_4$ linear or branched saturated hydrocarbon groups such as ethylene and isopropylene; and $C_5$-$C_{14}$ saturated alicyclic hydrocarbon groups having a cyclohexane ring, norbornane ring, 7-oxa-norbornane ring, 7-thia-norbornane ring, adamantane ring or tetracyclo[4.4.0.1$^{2,5}$.1$^{7,10}$]dodecane ring, which may comprise an oxygen atom and/or sulfur atom. The cyclohexane ring, norbornane ring and adamantane ring are preferred. $R_{15}$ represents a single bond, or $C_1$-$C_4$ divalent hydrocarbon group which may be substituted with a fluorine atom(s), and specific examples of $R_{15}$ include a single bond and $C_1$-$C_4$ alkylene which may be substituted with a fluorine atom(s), such as methylene, 1,1-ethylene, 2,2-propylene, 1,1,1,3,3,3-hexafluoro-2,2-propylene and 1,1,1-trifluoro-2-trifluoromethyl-2,3-propylene. $R_{15}$ is preferably a single bond, 1,1,1,3,3,3-hexafluoro-2,2-propylene or 1,1,1-trifluoro-2-trifluoromethyl-2,3-propylene. The combination wherein $R_{14}$ is adamantyl and $R_{15}$ is a single bond is especially preferred. j represents an integer of 1 to 3.

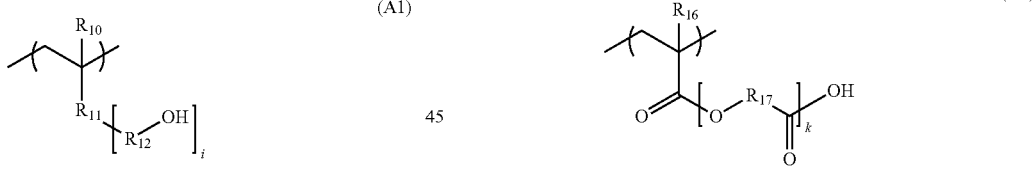

(A3)

In Formula (A3), $R_{16}$ represents a hydrogen atom, or $C_1$-$C_4$ hydrocarbon group which may be substituted with a fluorine atom(s), and specific examples of $R_{16}$ include a hydrogen atom; and $C_1$-$C_4$ alkyl which may be substituted with a fluorine atom(s), such as methyl, ethyl, n-propyl, i-propyl, n-butyl, i-butyl and trifluoromethyl. $R_{16}$ is preferably a hydrogen atom, methyl or trifluoromethyl. $R_{17}$ represents a $C_6$-$C_{12}$ divalent alicyclic hydrocarbon group which may comprise an oxygen atom and/or sulfur atom, and specific examples of $R_{17}$ include alicyclic hydrocarbon groups having a norbornane ring, 7-oxa-norbornane ring, 7-thia-norbornane ring, tetracyclo[4.4.0.1$^{2,5}$.1$^{7,10}$]dodecane ring and/or the like, which may comprise an oxygen atom and/or sulfur atom. The norbornane ring and tetracyclo[4.4.0.1$^{2,5}$.1$^{7,10}$]dodecane ring are preferred. k represents an integer of 0 or 1.

Specific examples of the repeating unit (A) are described below, but these examples do not limit the present invention. One type, or a plurality of types having different structures may be selected from the examples of the repeating unit (A).

(A101) 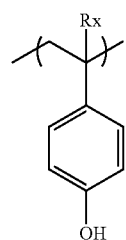
(A102) 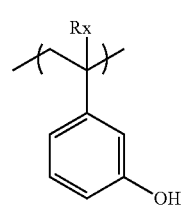
(A103) 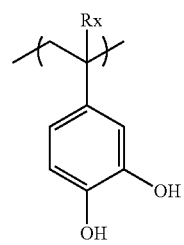
(A104) 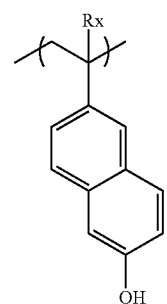
(A105) 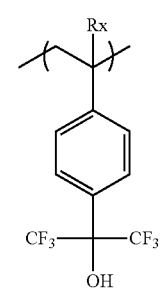
(A201) 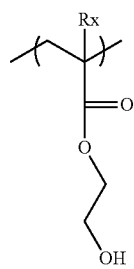
(A202) 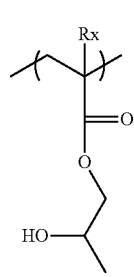
(A203) 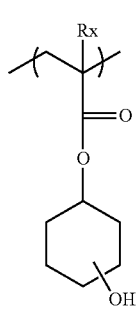
(A204) 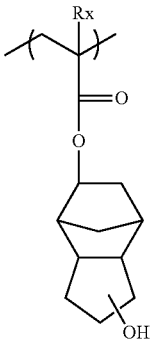
(A205) 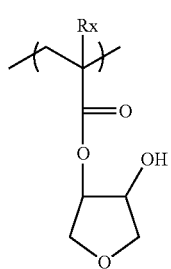
Wherein Rx represents H, $CH_3$ or $CF_3$.

-continued
(A206) 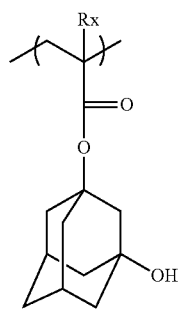
(A207) 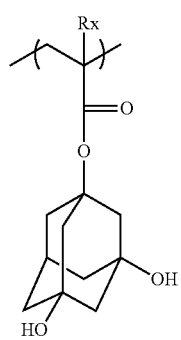
(A208) 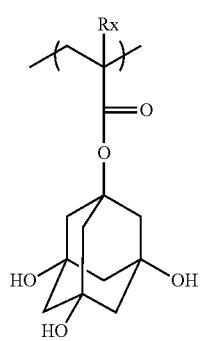
(A209) 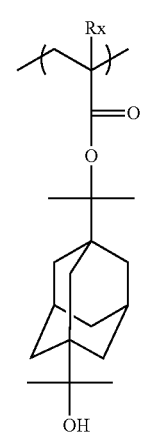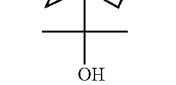
(A210) 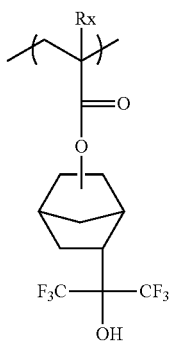
(A211) 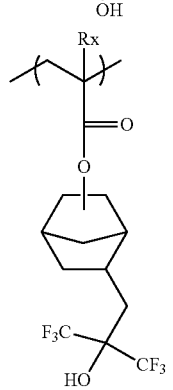
(A301) 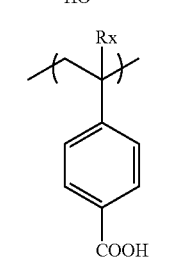
(A302) 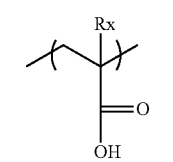
(A303) 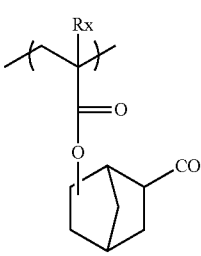
(A304) 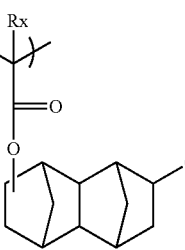
Wherein Rx represents H, CH$_3$ or CF$_3$.

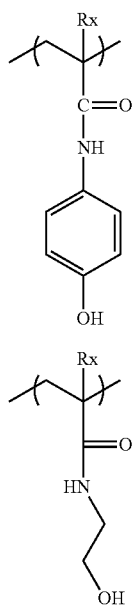

(A401)

(A402)

Wherein Rx represents H, CH$_3$ or CF$_3$.

Repeating Unit (B)

The repeating unit (B) is a repeating unit having a structure wherein an OH group is protected with an acid-dissociable, dissolution inhibiting group, and has a function to change the solubility of the polymer to an alkaline developer. Preferred examples of the repeating unit (B) include a structure wherein an OH group in a structure represented by any of Formulae (A1) to (A3) is protected with an acid-dissociable, dissolution inhibiting group represented by Formula (b1) or (b2).

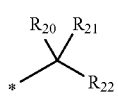

(b1)

In Formula (b1), * represents the position of linkage of Formula (b1) itself; $R_{20}$ and $R_{21}$ each independently represents a $C_1$-$C_4$ hydrocarbon group, and specific examples of each of $R_{20}$ and $R_{21}$ include $C_1$-$C_4$ alkyl such as methyl, ethyl, n-propyl, i-propyl, n-butyl and i-butyl. $R_{22}$ represents a $C_1$-$C_{12}$ hydrocarbon group, and specific examples of $R_{22}$ include $C_1$-$C_{12}$ linear, branched or cyclic alkyl such as methyl, ethyl, n-propyl, i-propyl, n-butyl, i-butyl, cyclopentyl, cyclohexyl, norbornyl, tricyclo[5.2.1.0$^{2,6}$]decanyl, adamantyl and tetracyclo[4.4.0.1$^{2,5}$.1$^{7,10}$]dodecanyl; and $C_6$-$C_{12}$ aryl such as phenyl and naphthyl. $R_{22}$ may be linked to $R_{20}$ or $R_{21}$ to form a ring, more particularly, a $C_5$-$C_{12}$ alicyclic ring such as a cyclopentane ring, cyclohexane ring, norbornane ring, tricyclo[5.2.1.0$^{2,6}$]decane ring, adamantane ring or tetracyclo[4.4.0.1$^{2,5}$.1$^{7,10}$]dodecane ring. Especially in cases where $R_{22}$ comprises, or in cases where $R_{22}$ is linked to $R_{20}$ or $R_{21}$ to form, a saturated alicyclic ring, more particularly, a cyclopentane ring, cyclohexane ring, norbornane ring, tricyclo[5.2.1.0$^{2,6}$]decane ring, adamantane ring or tetracyclo[4.4.0.1$^{2,5}$.1$^{7,10}$]dodecane ring, the solubilities to an alkaline developer before and after lithography are largely different from each other, which is preferred for drawing a fine pattern.

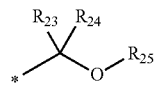

(b2)

In Formula (b2), * represents the position of linkage of Formula (b2) itself; $R_{23}$ and $R_{24}$ each independently represents a hydrogen atom or $C_1$-$C_4$ hydrocarbon group, and specific examples of each of $R_{23}$ and $R_{24}$ include a hydrogen atom; and $C_1$-$C_4$ alkyl such as methyl, ethyl, n-propyl, i-propyl, n-butyl and i-butyl. $R_{25}$ represents a $C_1$-$C_{12}$ hydrocarbon group, and specific examples thereof include $C_1$-$C_{12}$ linear, branched or cyclic alkyl such as methyl, ethyl, n-propyl, i-propyl, n-butyl, i-butyl, t-butyl, 2-ethylhexyl, cyclopentyl, cyclohexyl, norbornyl, tricyclo[5.2.1.0$^{2,6}$]decanyl, adamantyl and tetracyclo[4.4.0.1$^{2,5}$.1$^{7,10}$]dodecanyl. $R_{23}$ may be linked to $R_{24}$ or $R_{25}$ to form a ring. Specific examples of the ring formed by linking of $R_{23}$ to $R_{24}$ include a cyclopentane ring, cyclohexane ring, norbornane ring, tricyclo[5.2.1.0$^{2,6}$]decane ring, adamantane ring or tetracyclo[4.4.0.1$^{2,5}$.1$^{7,10}$]dodecane ring, and specific examples of the ring formed by linking of $R_{23}$ to $R_{25}$ include a hydrofuran ring and hydropyran ring.

Specific examples of the repeating unit (B) are described below, but these examples do not limit the present invention. One type or a plurality of types having different structures may be selected from the examples of the repeating unit (B).

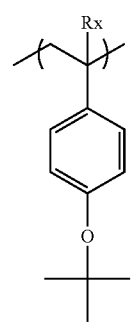

(B101)

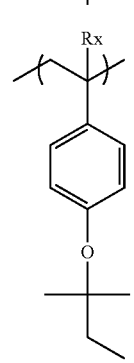

(B102)

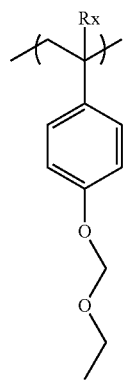 (B103)
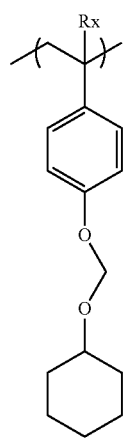 (B104)
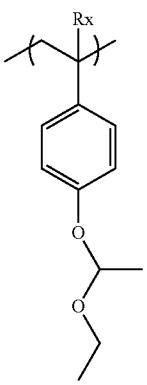 (B105)
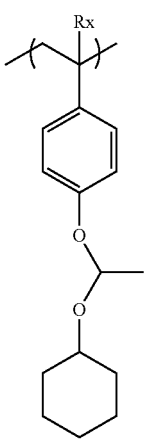 (B106)
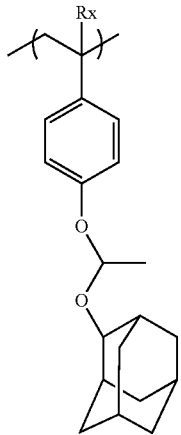 (B107)
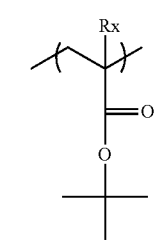 (B201)
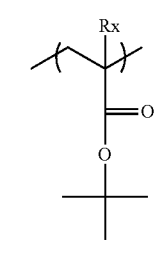 (B202)
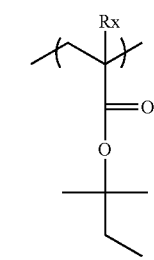 (B203)
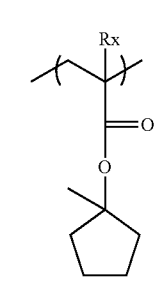 (B204)

(B205) 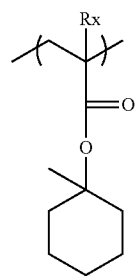
(B206) 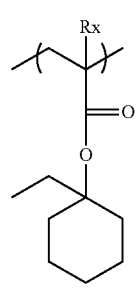
(B207) 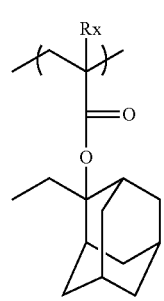
(B208) 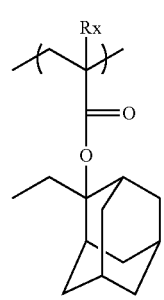
(B209) 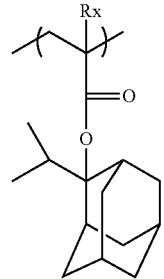
(B210) 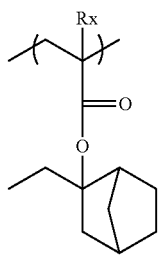
(B211) 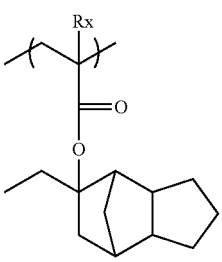
(B212) 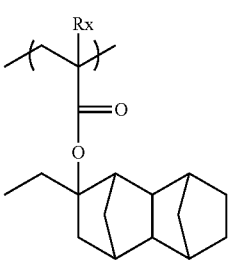
(B213) 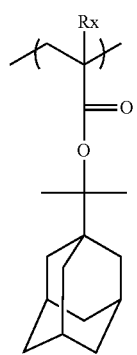
(B214) 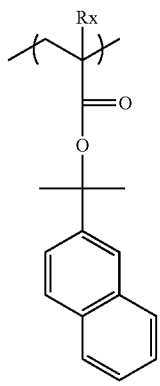
Wherein Rx represents H, CH$_3$ or CF$_3$.

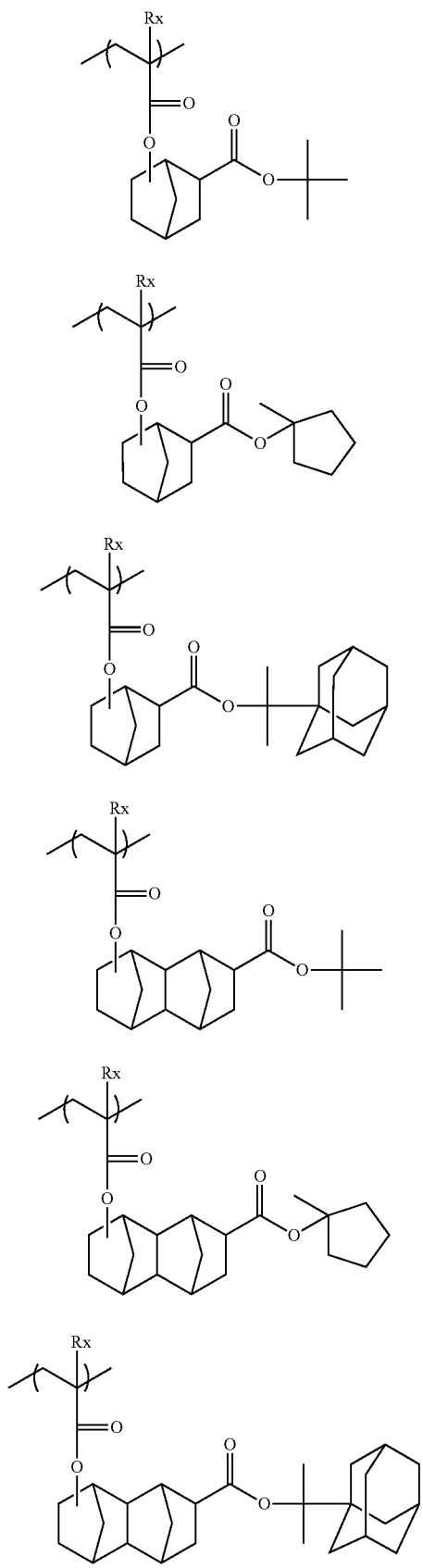
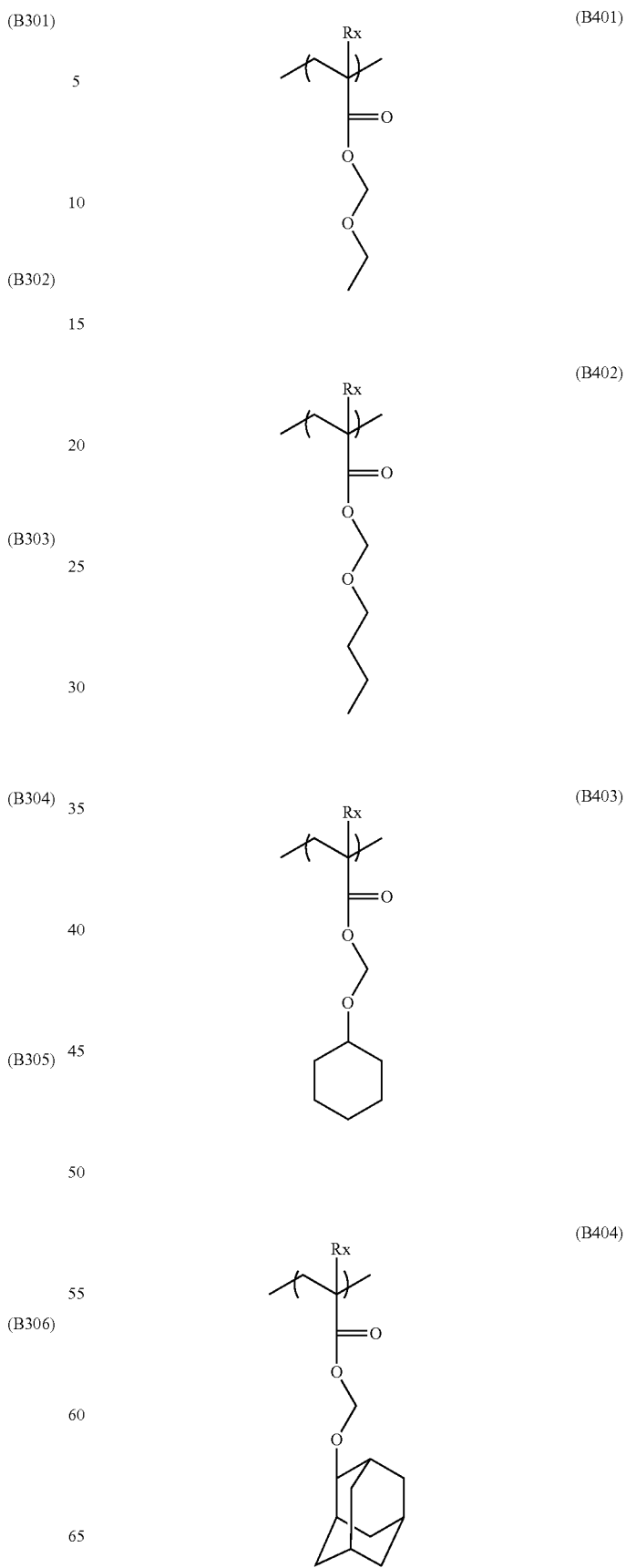

(B405) 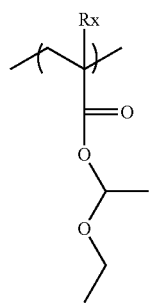
(B406) 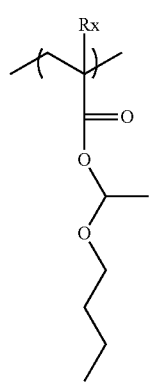
(B407) 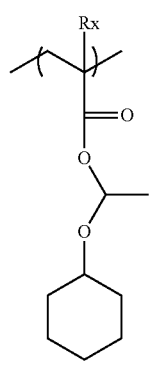
(B408) 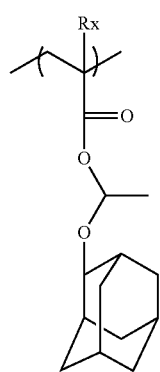
(B409) 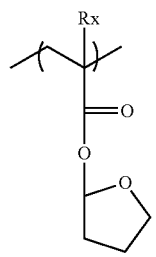
(B410) 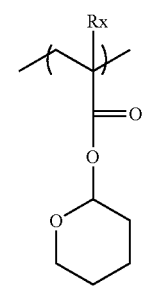
(B411) 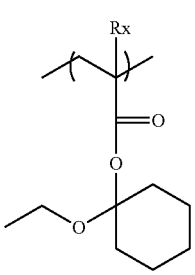
(B412) 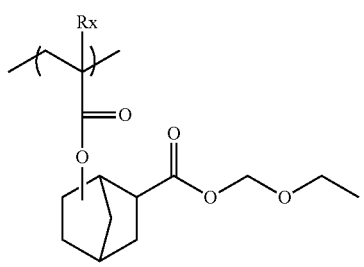
(B413) 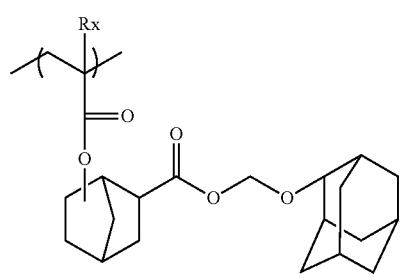
(B414) 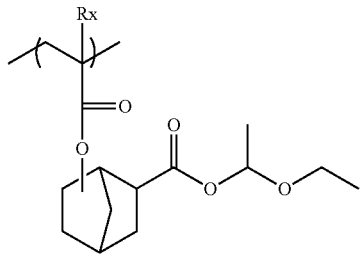

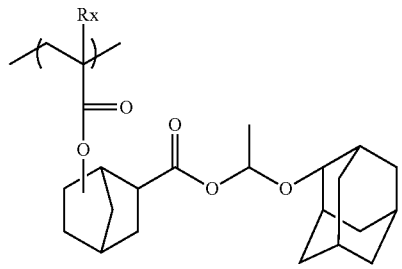
(B415)

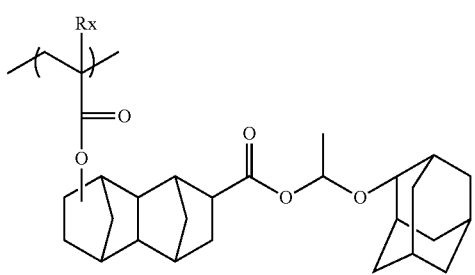
(B416)

Wherein Rx represents H, CH$_3$ or CF$_3$.

Repeating Unit (C)

The repeating unit (C) is a repeating unit having a lactone structure, and enhances adhesion of the polymer to a substrate or bed layer, and controls the solubility to a lithography solvent or alkaline developer. Preferred examples of the repeating unit (C) include structures represented by Formula (C1).

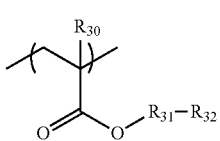
(C1)

In Formula (C1), $R_{30}$ represents a hydrogen atom, or $C_1$-$C_4$ hydrocarbon group which may be substituted with a fluorine atom(s), and specific examples of $R_{30}$ include a hydrogen atom, and $C_1$-$C_4$ alkyl such as methyl, ethyl, n-propyl, i-propyl, n-butyl, i-butyl and trifluoromethyl. $R_{30}$ is preferably a hydrogen atom, methyl or trifluoromethyl. $R_{31}$ represents a single bond or divalent linking group. The divalent linking group may be $C_1$-$C_4$ alkylene or a group in which the alkylene is substituted with an oxygen atom(s), carbonyl and/or carbonyloxy. $R_{32}$ is a lactone structure-containing group represented by Formula (c).

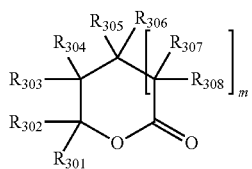
(c)

In Formula (c), any one of $R_{301}$ to $R_{308}$ represents a single bond which is the position of linkage of $R_{32}$ itself, and each of the remaining $R_{301}$ to $R_{308}$ represents a hydrogen atom, $C_1$-$C_4$ hydrocarbon group or alkoxy; or any one of $R_{301}$ to $R_{308}$ represents a $C_3$-$C_{14}$ hydrocarbon group that comprises the position of linkage of $R_{32}$ itself and is linked to any one or two of the other $R_{301}$ to $R_{308}$ to form a $C_5$-$C_{15}$ alicyclic ring, which $C_3$-$C_{14}$ hydrocarbon group may comprise an oxygen atom and/or sulfur atom, each of any one or two of the remaining $R_{301}$ to $R_{308}$ represents a single bond for formation of the $C_5$-$C_{15}$ alicyclic ring, and each of the other $R_{301}$ to $R_{308}$ represents a hydrogen atom, $C_1$-$C_4$ hydrocarbon group or alkoxy. m represents an integer of 0 or 1.

Specific examples of the above alicyclic ring include a cyclopentane ring, cyclohexane ring, norbornane ring, 7-oxa-norbornane ring, 7-thia-norbornane ring and tetracyclo [4.4.0.1$^{2,5}$.1$^{7,10}$]dodecane ring, and the alicyclic ring is preferably a norbornane ring or 7-oxa-norbornane ring. Specific examples of the $C_1$-$C_4$ hydrocarbon group include methyl, ethyl, n-propyl, i-propyl, n-butyl and i-butyl, and specific examples of the $C_1$-$C_4$ alkoxy include methoxy and ethoxy.

In Formula (c), especially preferred examples of the lactone structure wherein any one of $R_{301}$ to $R_{308}$ represents a single bond having the position of linkage of $R_{32}$ itself and each of the remaining $R_{301}$ to $R_{308}$ represents a hydrogen atom, $C_1$-$C_4$ hydrocarbon group or alkoxy include the γ-butyrolactone structure and δ-valerolactone structure. Especially preferred examples of the lactone structure wherein any one of $R_{301}$ to $R_{308}$ represents a $C_3$-$C_{14}$ hydrocarbon group that comprises the position of linkage of $R_{32}$ itself and is bound to any one or two of the other $R_{301}$ to $R_{308}$ to form a $C_5$-$C_{15}$ alicyclic ring, which $C_3$-$C_{14}$ hydrocarbon group may comprise an oxygen atom and/or sulfur atom, and each of the other $R_{301}$ to $R_{308}$ represents a hydrogen atom, $C_1$-$C_4$ hydrocarbon group or alkoxy include the 1,3-cyclohexanecarbolactone structure, 2,6-norbornanecarbolactone structure, 7-oxa-2,6-norbornanecarbolactone structure and 4-oxa-tricyclo [5.2.1.0$^{2,6}$]decane-3-one structure.

Specific examples of the repeating unit (C) are described below, but these examples do not limit the present invention. One type, or a plurality of types having different structures may be selected from the examples of the repeating unit (C).

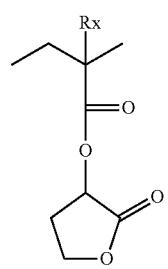
(C301)

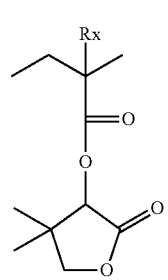
(C302)

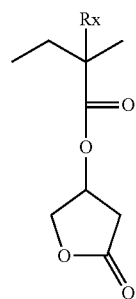 (C303)
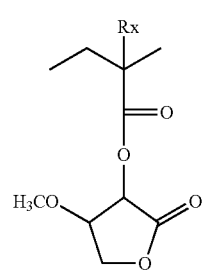 (C304)
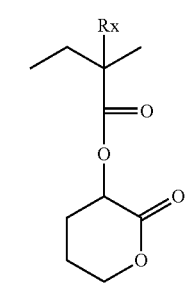 (C305)
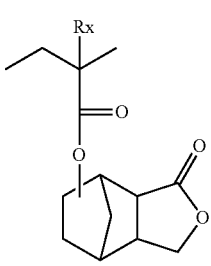 (C306)
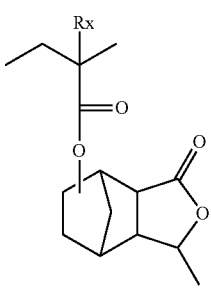 (C307)
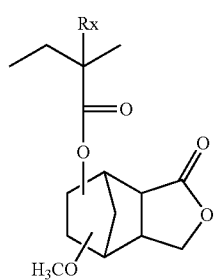 (C308)
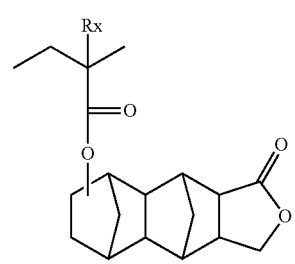 (C309)
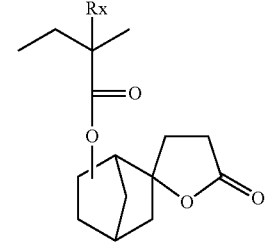 (C310)
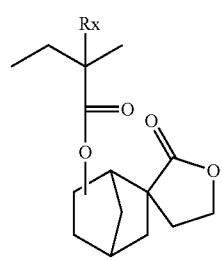 (C311)
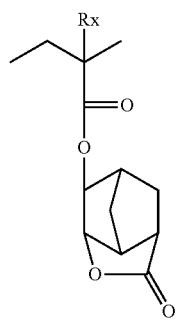 (C312)

(C313) 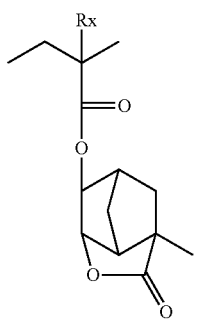

(C314) 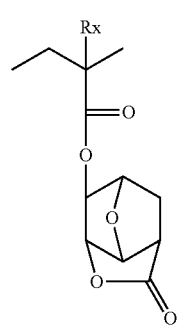

(C315) 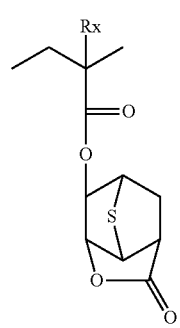

(C316) 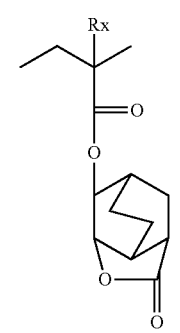

(C317) 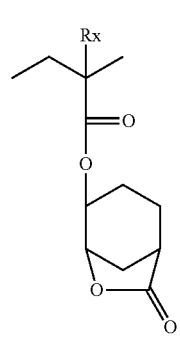

(C318) 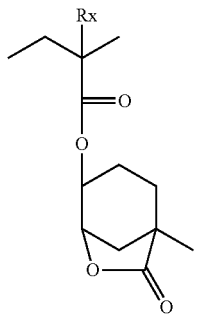

(C319) 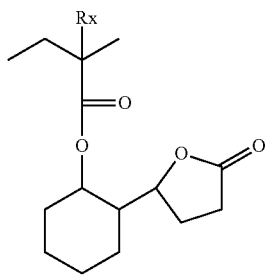

(C401) (C402) 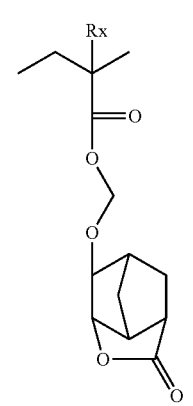

Wherein Rx represents H, $CH_3$ or $CF_3$.

Repeating Unit (D)

The repeating unit (D) is a repeating unit having a cyclic ether structure, and enhances adhesion of the polymer to a substrate or bed layer, controls the solubility to a lithography solvent or alkaline developer, and gives a function to react with a curing agent to form a cross-linking structure. Preferred examples of the repeating unit (D) include structures represented by Formula (D1).

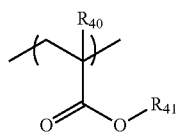
(D1)

In Formula (D1), $R_{40}$ represents a hydrogen atom, or $C_1$-$C_4$ hydrocarbon group which may be substituted with a fluorine atom(s), and specific examples of $R_{40}$ include a hydrogen atom, and $C_1$-$C_4$ alkyl such as methyl, ethyl, n-propyl, i-propyl, n-butyl, i-butyl and trifluoromethyl. $R_{40}$ is preferably a hydrogen atom, methyl or trifluoromethyl. $R_{41}$ represents a $C_3$-$C_7$ hydrocarbon group comprising a 3- to 6-membered cyclic ether structure, more particularly, a hydrocarbon group having an epoxy ring, oxetane ring, tetrahydrofuran ring or tetrahydropyran ring, still more particularly, glycidyl, oxetanylmethyl, tetrahydrofuranylmethyl or tetrahydropyranylmethyl. Glycidyl is especially preferred.

Specific examples of the repeating unit (D) are described below, but these examples do not limit the present invention. One type, or a plurality of types having different structures may be selected from the examples of the repeating unit (D).

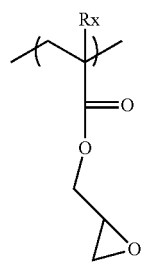
(D101)

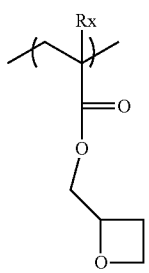
(D102)

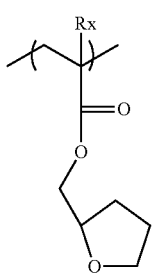
(D103)

wherein Rx represents H, $CH_3$ or $CF_3$.

Repeating Unit (E)

The repeating unit (E) is an acid-stable, dissolution inhibiting group, which is not dissociated by the action of an acid, and has a structure wherein a hydroxyl group or carboxy group is protected. This unit gives functions to control the solubility to a lithography solvent or alkaline developer, and optical properties of the thin film such as the refractive index and the light transmittance. Preferred examples of this unit include the repeating units (E1), (E2) and (E3), wherein the hydrogen atom of the hydroxyl group in the monomers represented as Formula (A1), Formula (A2) and Formula (A3), respectively, is replaced with an acid-stable, dissolution inhibiting group.

Examples of the acid-stable, dissolution inhibiting group of the repeating units (E1) to (E3) include a $C_1$-$C_{12}$ aliphatic hydrocarbon group wherein the carbon which substitutes the hydrogen atom of the OH group and is linked to the oxygen atom is a primary or secondary carbon; aromatic hydrocarbon group; and structures wherein methyl and/or 1-adamantyl is/are linked. Specific examples of the acid-stable, dissolution inhibiting group include methyl, ethyl, n-propyl, i-propyl, n-butyl, i-butyl, cyclopentyl, cyclohexyl, 2-norbornyl, 2-isobornyl, 8-tricyclo[5.2.1.0$^{2,6}$]decanyl, 1-adamantyl, 2-adamantyl, 4-tetracyclo[4.4.0.1$^{2,5}$.1$^{7,10}$]dodecanyl, phenyl, benzyl, naphthyl and anthracenyl.

Another preferred example is a repeating unit represented by Formula (E4).

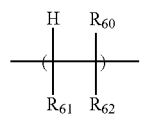
(E4)

In Formula (E4), $R_{60}$ represents a hydrogen atom, or $C_1$-$C_4$ hydrocarbon group which may be substituted with a fluorine atom(s), and specific examples of $R_{60}$ include a hydrogen atom; and $C_1$-$C_4$ alkyl which may be substituted with a fluorine atom(s), such as methyl, ethyl, n-propyl, i-propyl, n-butyl, i-butyl and trifluoromethyl. $R_{60}$ is preferably a hydrogen atom, methyl or trifluoromethyl. $R_{61}$ represents a hydrogen atom, or a single bond or $C_1$-$C_4$ alkylene linked to $R_{62}$, and specific examples of $R_{61}$ include a hydrogen atom, single bond, methylene, ethylene and isopropylene. $R_{62}$ is a $C_6$-$C_{14}$ aromatic hydrocarbon group, and specific examples of $R_{62}$ include a benzene ring, naphthalene ring and anthracene ring.

Specific examples of the repeating unit (E) are described below, but these examples do not limit the present invention. One type, or a plurality of types having different structures may be selected from the examples of the repeating unit (E).

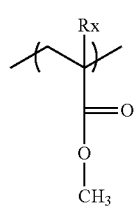
(E101)

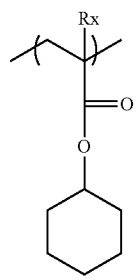 (E102)
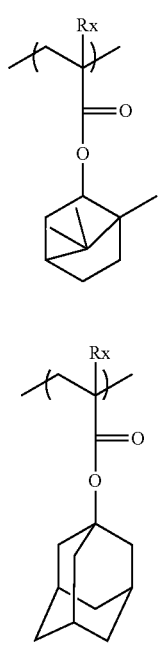
(E103)
(E104)
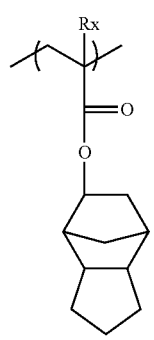 (E105)
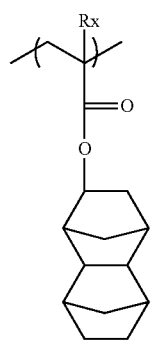 (E106)
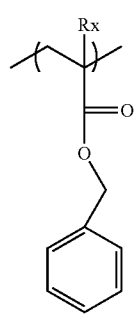 (E107)
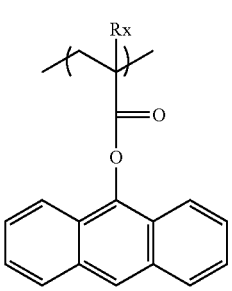 (E108)
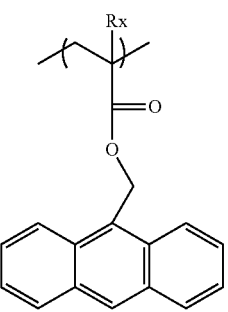 (E109)
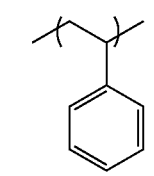 (E201)
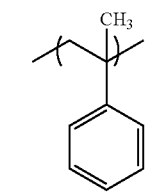 (E202)
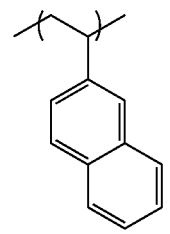 (E203)

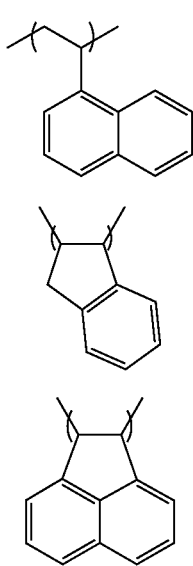

(E204)

(E205)

(E206)

Wherein Rx represents H, CH$_3$ or CF$_3$.

The composition of each repeating unit varies depending on the object of use of the thin film in semiconductor lithography. The followings are examples of the composition ranges of the repeating units in each object of use of the thin film.

In cases where the thin film is used for a chemical amplification positive resist film, the total amount of the repeating unit (A) and the repeating unit (C) is selected within the range of 20 to 95 mol %, preferably 30 to 90 mol %, more preferably 40 to 85 mol %; the amount of the repeating unit (B) is selected within the range of 5 to 80 mol %, preferably 10 to 70 mol %, more preferably 15 to 60 mol %; and the amount of the repeating unit (E) is selected within the range of 0 to 50 mol %, preferably 0 to 40 mol %, more preferably 0 to 30 mol %.

In cases where the thin film is used for a negative resist film, the total amount of the repeating unit (A) and the repeating unit (D) is selected within the range of 50 to 100 mol %, preferably 60 to 100 mol %, more preferably 70 to 100 mol %; the amount of the repeating unit (C) is selected within the range of 0 to 50 mol %, preferably 0 to 40 mol %, more preferably 0 to 30 mol %; and the amount of the repeating unit (E) is selected within the range of 0 to 50 mol %, preferably 0 to 40 mol %, more preferably 0 to 30 mol %.

In cases where the thin film is used for an antireflection coating or an immersion topcoat, the total amount of the repeating unit (A) and the repeating unit (D) is selected within the range of 5 to 80 mol %, preferably 10 to 70 mol %, more preferably 15 to 60 mol %; the amount of the repeating unit (B) is selected within the range of 0 to 50 mol %, preferably 0 to 40 mol %, more preferably 0 to 30 mol %; the amount of the repeating unit (C) is selected within the range of 0 to 50 mol %, preferably 0 to 40 mol %, more preferably 0 to 30 mol %; and the amount of the repeating unit (E) is selected within the range of 0 to 95 mol %, preferably 10 to 90 mol %, more preferably 20 to 85 mol %.

Polymerization Step

The polymerization step of the present invention is a step wherein the monomers that give the repeating units of the above copolymer are subjected to radical polymerization in an organic solvent in the presence of a radical polymerization initiator, and can be carried out by a known method. Examples of the method include the simultaneous heating method, in which monomers as well as a polymerization initiator are dissolved in a solvent and the resulting solution is heated as it is to allow polymerization; and the dropping polymerization method, in which monomers and a polymerization initiator are added dropwise to a heated solvent to allow polymerization. Further, examples of the dropping polymerization method include the mixture dropping method, in which monomers are dissolved as required in a solvent together with a polymerization initiator, and the resulting solution is added dropwise to a heated solvent to allow polymerization; and the independent dropping method, in which monomers and a polymerization initiator are separately dissolved as required in solvents and the resulting solutions are separately added dropwise to a heated solvent. In the present invention, the dropping polymerization method is preferred.

Since unreacted monomers at a high concentration have chances to contact with radicals at a low concentration in the polymerization system in the case of the simultaneous heating method, or in the storage tank containing the solution before being added dropwise to the polymerization system in the case of the mixture dropping method, high polymers having molecular weights of not less than 100,000, which are one of the causes of pattern defects, are likely to be produced. On the other hand, in the independent dropping method, a polymerization initiator and monomers do not coexist in the storage tank for the solution to be dropped, and the concentration of unreacted monomers can be kept low even after their addition to the polymerization system. Therefore, high polymers are not likely to be produced, and hence the independent dropping method is especially preferred as the polymerization method in the present invention. In the mixture dropping method and the independent dropping method, the drop time; the composition of monomers; the composition ratio among monomers, polymerization initiator and chain transfer agent; and/or the like, may be changed.

As described above, the polymerization initiator is allowed to pass through a filter having a nominal pore size of not more than 1.0 μm before being used to remove metals. The amount of the polymerization initiator to be used may be selected based on the desired molecular weight; types of monomers, polymerization initiator, chain transfer agent, solvent and/or the like; composition of repeating units; polymerization temperature; drop rate; and/or the like.

In terms of the chain transfer agent, a known chain transfer agent may be employed as required. A thiol compound is especially preferred, and may be selected from a wide variety of known thiol compounds. Specific examples of the thiol compound include t-dodecylmercaptan, mercaptoethanol, mercaptoacetic acid and mercaptopropionic acid. Further, a thiol compound having a structure in which 2-hydroxy-1,1,1,3,3,3-hexafluoro-2-propyl is linked to a saturated aliphatic hydrocarbon is especially preferred since it has an effect to suppress roughness and defects of lithographic patterns. The amount of the chain transfer agent to be used may be selected based on the desired molecular weight; types of monomers, polymerization initiator, chain transfer agent, solvent and/or the like; composition of repeating units; polymerization temperature; drop rate; and/or the like.

In cases where the monomers and the polymerization initiator themselves in the solution to be dropped are liquids, those may be supplied as they are without being dissolved in a solvent, but, in cases where the monomers and/or polymerization initiator is/are in the form(s) of a viscous liquid(s) or solid(s), the monomers and/or polymerization initiator need(s) to be dissolved in a solvent. The concentrations of the monomers and the polymerization initiator are preferably high in view of productivity, but in cases where the concentrations are too high, the operability is poor because of high solution viscosity, and in cases where the monomers or the polymerization initiator is/are solid, these may be precipitated, and/or their diffusion in the polymerization system takes time, so that high polymers may be likely to be produced. Therefore, it is preferred to select a concentration at which the viscosity is within the range where the supplying operation can be carried out without any problem; and at which each monomer and the polymerization initiator are sufficiently dissolved, do not precipitate while they are supplied, and are easily diffused in the polymerization system. The specific concentration varies depending on the combination of the solute and the solvent of each solution, and the like, and each solution is prepared such that each of the total concentration of all the monomers and the concentration of the polymerization initiator is, for example, within the range of 5 to 60% by weight, preferably 10 to 50% by weight.

In cases where a monomer solution at a low temperature is added dropwise to the polymerization system, an environment is locally generated in which the temperature is low, the monomer concentration is high and the radical concentration is low. Such an environment may lead to production of high polymers and is therefore not preferred. Thus, the monomer solution is preferably preheated before being supplied.

Examples of the method for preheating the monomer solution include a method in which the monomer solution is heated with a heat exchanger or the like immediately before being supplied to the storage tank or the polymerization system. The temperature for the preheating is preferably not less than 25° C., more preferably not less than 30° C. However, in cases where the monomer solution is preheated in the storage tank, the solution is kept in a heated state for a long time, so that, if the temperature is high, high polymers may be produced. Therefore, in cases where the monomer solution is preheated in the storage tank, the temperature is preferably set to not more than 50° C., more preferably not more than 40° C. It is also possible to preheat the initiator solution, but, in cases where the temperature is high, the polymerization initiator is decomposed before being supplied. Therefore, the temperature is usually set to not more than 40° C., preferably not more than 30° C., more preferably not more than 25° C.

If the drop time in the mixture dropping method and the independent dropping method is short, a broad molecular weight distribution is likely to be obtained, and, since a large amount of the solution is added dropwise at once, the temperature of the polymerization solution decreases, which is not preferred. On the other hand, if the drop time is long, the thermal history of the copolymer is unnecessarily long, leading to decrease in the productivity, which is not preferred. Therefore, the drop time is usually selected within the range of 0.5 to 24 hours, preferably 1 to 12 hours, especially preferably 2 to 8 hours.

Further, after completion of the dropping, and after increasing the temperature to the polymerization temperature in the simultaneous heating method, it is preferred, for example, to maintain the temperature for a certain period of time or further increase the temperature, to perform maturation, thereby reacting the remaining unreacted monomers. In cases where the maturation time is too long, the production efficiency per unit time is low, and the thermal history of the copolymer is unnecessarily long, which is not preferred. Therefore, the maturation time is usually selected within the range of not more than 12 hours, preferably not more than 6 hours, especially preferably 1 to 4 hours.

The solvent to be used in the polymerization reaction is not restricted as long as the solvent can stably dissolve raw material monomers, obtained copolymer, polymerization initiator and chain transfer agent. Specific examples of the polymerization solvent include water; ketones such as acetone, methyl ethyl ketone, methyl isobutyl ketone, methyl isoamyl ketone, methyl amyl ketone and cyclohexanone; alcohols such as methanol, ethanol and isopropanol; ether alcohols such as ethylene glycol monomethyl ether, ethylene glycol monoethyl ether, propylene glycol monomethyl ether and propylene glycol monoethyl ether; esters such as methyl acetate, ethyl acetate, isopropyl acetate, propyl acetate, butyl acetate, methyl propionate, methyl lactate and ethyl lactate; ether esters such as ethylene glycol monomethyl ether acetate, ethylene glycol monoethyl ether acetate, propylene glycol monomethyl ether acetate and propylene glycol monoethyl ether acetate; ethers such as tetrahydrofuran, 1,4-dioxane and ethylene glycol dimethyl ether; aromatic hydrocarbons such as toluene and xylene; N,N-dimethylformamide; and acetonitrile. In views of the solubilities of the monomers, polymerization initiator, chain transfer agent and copolymer, and of the boiling point, acetone, methyl ethyl ketone, methyl isobutyl ketone, isopropanol, propylene glycol monomethyl ether, methyl acetate, ethyl acetate, isopropyl acetate, propyl acetate, methyl propionate, tetrahydrofuran, 1,4-dioxane, ethylene glycol dimethyl ether, toluene and acetonitrile are preferred. These may be used either alone or as a mixture of two or more thereof. Further, these may be used as a mixture with a compound in which the monomers, polymerization initiator, chain transfer agent and copolymer are highly soluble and which has a high boiling point. Examples of the compound include ethylene glycol monobutyl ether, 3-methoxy-3-methyl-1-butanol, 3-methoxy-3-methyl-1-butyl acetate, 3-ethoxy ethyl propionate, γ-butyrolactone, diethylene glycol dimethyl ether, N-methyl pyrrolidone and dimethyl sulfoxide.

The amount of the polymerization solvent to be used is not restricted, and in cases where the amount of the solvent used is too small, monomers may be precipitated and/or the viscosity of the solution is too high to keep the polymerization system uniform. In cases where the amount of the solvent used is too large, there are cases where the degree of conversion of the monomers is insufficient and/or the molecular weight of the copolymer cannot be increased to the desired value. The amount of the polymerization solvent to be used is normally 0.5 to 20 parts by weight, preferably 1 to 10 parts by weight with respect to 1 part by weight of monomers.

The amount of the polymerization solvent to be initially filled in the reaction vessel (which may be hereinafter referred to as the initially filled solvent) in the mixture dropping method and the independent dropping method is sufficient as long as the amount is not less than the lowest amount at which the resulting solution can be stirred, while in cases where the amount is unnecessarily large, the amount of the monomer solution which can be supplied is small and hence the production efficiency is low, which is not preferred. The amount of the initially filled solvent is usually selected within the range of, for example, not less than 1/30, preferably 1/20 to 1/2, especially preferably 1/10 to 1/3, in terms of the volume ratio with respect to the final filled amount (that is, the total amount of the initially filled solvent, and the monomer solution and the initiator solution to be dropped). A part of the monomers may be preliminarily mixed with the initially filled solvent.

The polymerization temperature may be appropriately selected based on the boiling points of the solvent, monomers, chain transfer agent and the like; the half-life temperature of the polymerization initiator; and the like. At a low temperature, the polymerization hardly proceeds and hence there is the problem of productivity, while at an unnecessarily high temperature, there are problems in view of the stability of the monomers and the copolymer. Therefore, the polymerization temperature is preferably selected within the range of 40 to 160° C., especially preferably 60 to 120° C. Since the polymerization temperature largely influences the molecular weight of the copolymer and the copolymer composition, the temperature should be precisely controlled. On the other hand, the polymerization reaction is generally an exothermic reaction and hence the polymerization temperature tends to increase, so that it is difficult to keep the temperature constant. Thus, preferably, in the present invention, one or more types of compounds having boiling points close to the polymerization temperature of interest are included as a polymerization solvent(s) and the polymerization temperature is set to not less than the initial boiling points of the compounds. By this method, increase in the polymerization temperature can be suppressed by the latent heat of vaporization of the polymerization solvent(s).

The polymerization pressure may be appropriately set, but, since nitrogen gas in the case of the azo system or oxygen gas in the case of the peroxide system is generated when radicals are generated from the initiator, the polymerization is preferably performed under a pressure near atmospheric pressure by setting the polymerization system to be an open system, in order to suppress fluctuation of the polymerization pressure.

Polymerization Reactor

In the production method according to the present invention for producing a polymer for semiconductor lithography, a known polymerization reactor may be used. For example, the above dropping polymerization method is preferably performed with a polymerization reactor at least comprising: a storage tank for a solution comprising a polymerization initiator; a polymerization reaction vessel; and a filter placed in a channel connected from the storage tank to the polymerization reaction vessel, which filter has a nominal pore size of not more than 1.0 µm. Further, the polymerization reactor may comprise a storage tank for a solution comprising raw material monomers. By using such an apparatus, removal of metal impurities from the polymerization initiator and synthesis of the polymer can be carried out in the same apparatus at the same time, so that the procedure, time and cost required for the production process can be reduced.

Purification Step

The copolymer obtained by polymerization contains low molecular weight impurities such as the polymerization solvent, unreacted monomers, oligomers, polymerization initiator and chain transfer agent, and their reaction by-products, and these are preferably removed by the purification step. More particularly, the removal is carried out by diluting as required the polymerization reaction solution by addition of a good solvent and bringing the solution into contact with a poor solvent to precipitate the copolymer as a solid, to extract impurities into the poor solvent phase (hereinafter referred to as reprecipitation), or carried out by forming a liquid-liquid two-phase to extract impurities into the poor solvent phase. In cases where reprecipitation was carried out, further purification is possible by a step wherein the precipitated solid is separated from the poor solvent by a method such as filtration or decantation and then redissolved in a good solvent, followed by reprecipitation by further addition of a poor solvent, or by a step wherein the precipitated solid is washed with a poor solvent. In cases where the liquid-liquid two-phase separation was carried out, further purification is possible by removing the poor solvent phase by separation, adding a poor solvent to the obtained copolymer solution, and then performing reprecipitation or liquid-liquid two-phase separation. In terms of these operations, the same operation may be repeated, or different operations may be performed in combination.

Examples of the poor solvent used in this purification step include compounds having a hydroxyl group, such as water, ethanol, isopropanol, ethylene glycol and ethyl lactate; linear, branched or cyclic saturated hydrocarbons such as pentane, n-hexane, iso-hexane, n-heptane, cyclopentane and ethylcyclohexane; and aromatic hydrocarbons such as toluene and xylene. These solvents may be used either alone or as a combination of two or more of these solvents. Examples of the good solvent include the above-described polymerization solvents and the solvents exemplified for the later-described solvent for film formation. A mixture of a good solvent(s) and a poor solvent(s) may also be used.

The type and the amount of the poor solvent used in the purification step are not restricted as long as the copolymer can be separated from low molecular weight compounds, and may be appropriately selected depending on the solubility of the copolymer to the poor solvent, the type and the amount of the solvent used for polymerization, the type and the amount of impurities, and the like. In cases where the amount of the poor solvent is small, separation of impurities such as the polymerization solvent and unreacted monomers is insufficient, while use of a large amount of the poor solvent is not preferred in views of ease of handling and the cost since, for example, waste fluid increases. In general, the amount of the poor solvent is 0.5 to 50 times, preferably 1 to 20 times, more preferably 2 to 10 times the total amount of the polymerization reaction solution after dilution of a good solvent as required, in terms of the weight.

Since the temperature during the purification step largely influences the molecular weight and the molecular weight distribution of the copolymer; removal rates of the residual monomers, residual initiator and the like; various properties in lithography; and the like; the temperature needs to be strictly controlled. In cases where the temperature during the purification step is too low, the solubilities of impurities to the reprecipitation solvent and washing solvent are insufficient and hence and removal of impurities cannot be achieved sufficiently, resulting in inefficiency. On the other hand, in cases where the temperature is too high, the copolymer is eluted into the reprecipitation solvent and the washing solvent, leading to an unbalanced composition in the low molecular weight region of the copolymer and/or a low yield, which is not preferred. Thus, the purification step is preferably carried out at a temperature within the range of 0 to 40° C., preferably within the range of 0 to 30° C.

The thus purified copolymer may be dried and recovered as powder, or may be redissolved by addition of a good solvent before or after the drying, to be recovered as a solution. Examples of the good solvent used in the redissolving include the above-described polymerization solvents and the solvents exemplified for the later-described solvent for film formation.

After the purification, the solvent of the copolymer solution may be replaced with a solvent for film formation, which is suitable for the later-described lithography composition. The substitution is carried out by heating the copolymer solution under reduced pressure to evaporate low boiling point substances such as the solvent used for purification, and supplying a solvent for film formation to the resulting solution while evaporating the initial solvent and the supplied solvent at the same time. By removing low boiling point impurities such as the solvent used for purification, the copolymer can be prepared into a solution for film formation.

The temperature during the heating under reduced pressure is not restricted as long as the copolymer is not deteriorated at the temperature, and, usually, the temperature is preferably not more than 100° C., more preferably not more than 80° C., still more preferably not more than 70° C., especially preferably not more than 60° C.

In the replacement of the solvent, in cases where the amount of the solvent for film coating supplied later is too small, low boiling point compounds cannot be sufficiently removed, and in cases where the amount is too large, the substitution takes a long time and the thermal history of the copolymer is unnecessarily long, which is not preferred. The amount of the solvent to be supplied may be selected within the range of 1.05 to 10 times, preferably 1.1 to 5 times, especially preferably 1.2 to 3 times the necessary amount of the solvent for the finished solution.

The solvent for film formation is not restricted as long as the solvent can dissolve the copolymer, and usually selected in consideration of the boiling point, influences on the coating films of the semiconductor substrate and the like, and absorbance of the radiation used for lithography. Examples of solvents commonly used for film formation include propylene glycol monomethyl ether acetate, propylene glycol monomethyl ether, propylene glycol n-butyl ether, dipropylene glycol n-propyl ether, dipropylene glycol n-butyl ether, ethyl lactate, methyl amyl ketone, γ-butyrolactone, cyclohexanone and 4-methyl-2-pentanol.

In cases where the copolymer was recovered as powder, the copolymer may mixed with and dissolved in a solvent for film formation, to be finished as a solution for film formation.

Although, in the present invention, metal impurities in the copolymer can be largely reduced by removal of metals from the initiator, the step of removal of metal impurities from the copolymer may be additionally carried out as required. In this step, the copolymer solution is allowed to pass through a filter having cation-exchange capacity or a filter comprising a substance having a positive zeta potential, such as polyamide polyamine epichlorohydrin cationic resin. These steps may be carried out in combination.

Specific examples of the filter comprising a substance having a positive zeta potential, such as polyamide polyamine epichlorohydrin cationic resin, include Zeta Plus 40 QSH, Zeta Plus 020 GN and LifeASSURE EF Series (registered trademarks) manufactured by CUNO INC.

Further, in order to remove microgels such as high polymers, which may cause pattern defects of resists and hence are not preferred, the copolymer solution (or the solution for film formation) is preferably filtered through a filter. The filtration accuracy of the filter is not more than 0.2 µm, preferably not more than 0.1 µm, especially preferably not more than 0.05 µm. Examples of the material of the filter include polyolefins such as polyethylene and polypropylene, polar group-containing resins such as polyamide, polyester and polyacrylonitrile; and fluorine-containing resins such as polyethylene fluoride. The material of the filter is preferably polyamide. Examples of the polyamide filter include Ultipleat P-Nylon 66 and Ultipor N66 manufactured by Pall Corporation, and LifeASSURE PSN Series and LifeASSURE EF Series manufactured by CUNO INC (registered trademarks). Examples of the polyolefin filter include Microguard Plus HC10 and Optimizer D manufactured by Nihon Entegris K.K. These filters may be used either alone or as a combination of two or more of the filters.

EXAMPLES

Embodiments of the present invention are described more concretely by way of Examples below. However, the present invention is not restricted at all by those Examples. Unless otherwise specified, parts are by weight, hereinafter.

Example 1

As a polymerization initiator, 3 parts of dimethyl 2,2'-azobis(2-methylpropionate) (manufactured by Wako Pure Chemical Industries, Ltd.) was dissolved in 7 parts of methyl ethyl ketone to prepare a uniform solution, which was then allowed to pass through a polypropylene hollow fiber membrane filter having a nominal pore size of 0.01 µm (manufactured by CUNO INC; trade name, NanoSHIELD). The polymerization initiator solution thereafter was analyzed by ICP mass spectrometry using an ICP mass spectrometer (manufactured by Agilent Technologies, Inc.; trade name, Agilent 7500cs), and, as a result, the sodium concentration in the polymerization initiator solution was found to be 83 ppb with respect to the weight of the polymerization initiator.

Example 2

The polymerization initiator solution was allowed to pass through a filter in the same manner as in Example 1 except that a polyethylene membrane filter having a nominal pore size of 0.03 µm (manufactured by Nihon Entegris K.K.; trade name, 47 mm UPE Disk Filter) was used. The polymerization initiator solution thereafter was analyzed by ICP mass spectrometry in the same manner as in Example 1, and, as a result, the sodium concentration in the polymerization initiator solution was found to be 120 ppb with respect to the weight of the polymerization initiator.

Example 3

The polymerization initiator solution was allowed to pass through a filter in the same manner as in Example 1 except that a PTFE membrane filter having a nominal pore size of 0.2 µm (manufactured by WHATMAN; trade name, Puradisc Syringe Filters) was used. The polymerization initiator solution thereafter was analyzed by ICP mass spectrometry in the same manner as in Example 1, and, as a result, the sodium concentration in the polymerization initiator solution was found to be 143 ppb with respect to the weight of the polymerization initiator.

Example 4

The polymerization initiator solution was allowed to pass through a filter in the same manner as in Example 1 except that a polyethylene membrane filter having a nominal pore size of 0.5 µm (manufactured by Nihon Entegris K.K.; trade name, 47 mm UPE Disk Filter) was used. The polymerization initiator solution thereafter was analyzed by ICP mass spectrometry in the same manner as in Example 1, and, as a result, the sodium concentration in the polymerization initiator solution was found to be 180 ppb with respect to the weight of the polymerization initiator.

Example 5

The polymerization initiator solution was allowed to pass through a filter in the same manner as in Example 1 except that a PEFE membrane filter having a nominal pore size of 1.0 µm (manufactured by Millipore; trade name, Omnipore) was used. The polymerization initiator solution thereafter was analyzed by ICP mass spectrometry in the same manner as in Example 1, and, as a result, the sodium concentration in the polymerization initiator solution was found to be 280 ppb with respect to the weight of the polymerization initiator.

Example 6

The polymerization initiator solution was allowed to pass through a filter in the same manner as in Example 1 except that Zeta Plus filter 40 QSH having a nominal pore size of 0.2 µm (with ion-exchange capacity, manufactured by CUNO INC.) was used. The polymerization initiator solution thereafter was analyzed by ICP mass spectrometry in the same manner as in Example 1, and, as a result, the sodium concentration in the polymerization initiator solution was found to be 2 ppb with respect to the weight of the polymerization initiator.

Example 7

The polymerization initiator solution was allowed to pass through a filter in the same manner as in Example 1 except that Zeta Plus filter 020GN having a nominal pore size of 0.2 µm (with zeta potential, manufactured by CUNO INC.) was used. The polymerization initiator solution thereafter was analyzed by ICP mass spectrometry in the same manner as in Example 1, and, as a result, the sodium concentration in the polymerization initiator solution was found to be 6 ppb with respect to the weight of the polymerization initiator.

Example 8

As a polymerization initiator, 1 part of 2,2'-azobisisobutyronitrile (manufactured by JAPAN FINECHEM COMPANY, INC.) was dissolved in 8 parts of methyl ethyl ketone and 1 part of water to prepare a uniform solution, which was then allowed to pass through Zeta Plus filter 40 QSH having a nominal pore size of 0.2 µm (manufactured by CUNO INC., with ion-exchange capacity). As a result of analysis by ICP mass spectrometry in the same manner as in Example 1, the sodium concentration in the polymerization initiator solution was found to be 22 ppb with respect to the weight of the polymerization initiator.

Comparative Example 1

As a polymerization initiator, 3 parts of dimethyl 2,2'-azobis(2-methylpropionate) (manufactured by Wako Pure Chemical Industries, Ltd.) was dissolved in 7 parts of methyl ethyl ketone to prepare a uniform solution. This polymerization initiator solution was analyzed by ICP mass spectrometry in the same manner as in Example 1, and, as a result, the sodium concentration in the polymerization initiator solution was found to be 4600 ppb with respect to the weight of the polymerization initiator Comparative Example 2

The polymerization initiator solution was allowed to pass through a filter in the same manner as in Example 1 except that a PTFE membrane filter having a nominal pore size of 3 µm (manufactured by Millipore; trade name, Florinate) was used. The polymerization initiator solution thereafter was analyzed by ICP mass spectrometry in the same manner as in Example 1, and, as a result, the sodium concentration in the polymerization initiator solution was found to be 650 ppb with respect to the weight of the polymerization initiator.

Comparative Example 3

The polymerization initiator solution was allowed to pass through a filter in the same manner as in Example 1 except that a PTFE membrane filter having a nominal pore size of 10 µm (manufactured by Millipore; trade name, Omnipore) was used. The polymerization initiator solution thereafter was analyzed by ICP mass spectrometry in the same manner as in Example 1, and, as a result, the sodium concentration in the polymerization initiator solution was found to be 1067 ppb with respect to the weight of the polymerization initiator.

Comparative Example 4

As a polymerization initiator, 1 part of 2,2'-azobisisobutyronitrile (manufactured by JAPAN FINECHEM COMPANY, INC.) was dissolved in 9 parts of methyl ethyl ketone, to prepare a uniform solution. This polymerization initiator solution was analyzed by ICP mass spectrometry in the same manner as in Example 1, and, as a result, the sodium concentration in the polymerization initiator solution was found to be 6200 ppb with respect to the weight of the polymerization initiator Example 9

Production of γ-Butyrolactone Methacrylate/Glycidyl Methacrylate/Methyl Methacrylate/Anthracene Methyl Methacrylate Copolymer To prepare a drop solution 1A, 1.2 kg of γ-butyrolactone methacrylate, 0.9 kg of glycidyl methacrylate, 1.6 kg of methyl methacrylate and 0.7 kg of anthracene methyl methacrylate were dissolved in 4.4 kg of methyl ethyl ketone. The polymerization initiator solution obtained in Example 1 in an amount of 1.5 kg (polymerization initiator concentration, 30% by weight) was provided as a drop solution 1B. Into a glass-lined polymerization tank equipped with a stirrer and a condenser, 2.6 kg of methyl ethyl ketone was fed, and the atmosphere was replaced with nitrogen. The methyl ethyl ketone in the polymerization tank was heated to 80° C., and the drop solution 1A and the drop solution 1B kept at 25 to 30° C. were added dropwise from separate storage tanks using a metering pump at a constant rate for 4 hours to the polymerization tank kept at 79 to 81° C., to allow polymerization. Thereafter, the resulting polymer was further left to stand at 80 to 81° C. for 2 hours for aging, and then cooled to room temperature, to obtain a polymerization solution 1.

The polymerization solution 1 was analyzed by ICP mass spectrometry using an ICP mass spectrometer (manufactured by Agilent Technologies, Inc.; trade name, Agilent 7500cs), and, as a result, the sodium content was found to be 4.5 ppb.

Example 10

Production of 3-Hydroxy-1-Adamantyl Methacrylate/2-Methyl-2-Adamantyl Methacrylate/γ-Butyrolactone Methacrylate Copolymer To prepare a drop solution 2A, 1.2 kg of 3-hydroxy-1-adamantyl methacrylate, 2.8 kg of 2-methyl-2-adamantyl methacrylate and 1.8 kg of γ-butyrolactone methacrylate were dissolved in 6.5 kg of methyl ethyl ketone. The polymerization initiator solution obtained in Example 5 in an amount of 0.6 kg (polymerization initiator concentration, 30% by weight) was provided as a drop solution 2B. Into a glass-lined polymerization tank equipped with a stirrer and a condenser, 4.2 kg of methyl ethyl ketone was fed, and the atmosphere was replaced with nitrogen. The methyl ethyl ketone in the polymerization tank was heated to 80° C., and the drop solution 2A and the drop solution 2B kept at 25 to 30° C. were added dropwise from separate storage tanks using a metering pump at a constant rate for 4 hours to the polymerization tank kept at 79 to 81° C., to allow polymerization. Thereafter, the resulting polymer was further left to stand at 80 to 81° C. for 2 hours for aging, and then cooled to room temperature, to obtain a polymerization solution 2.

The polymerization solution 2 was analyzed by ICP mass spectrometry using an ICP mass spectrometer (manufactured by Agilent Technologies, Inc.; trade name, Agilent 7500cs), and, as a result, the sodium content was found to be 4.1 ppb.

Comparative Example 5

Operations were carried out in the same manner as in Example 9 except that the polymerization initiator solution in Comparative Example 2 was used instead. The sodium content in the obtained polymerization solution was found to be 28 ppb.

Operations were carried out in the same manner as in Example 10 except that the polymerization initiator solution in Comparative Example 1 was used instead. The sodium content in the obtained polymerization solution was found to be 55 ppb.

The invention claimed is:

1. A method for producing a polymer for semiconductor lithography, said polymer comprising at least one type of repeating units selected from the group consisting of a repeating unit having a hydroxy group or carboxy group (A), a repeating unit having a structure wherein a hydroxy group or carboxy group is protected with a group that suppresses dissolution into an alkaline developer and is dissociable by the action of an acid (B), a repeating unit having a lactone structure (C), and a repeating unit having a cyclic ether structure (D), said method comprising:
   a filtering step, wherein a solution of a polymerization initiator dissolved in an organic solvent is passed through a filter having a pore size of not more than 1.0 μm to reduce a sodium content of said polymerization initiator solution to not more than 300 ppb with respect to a weight of said polymerization initiator to produce a purified polymerization initiator; and
   a polymerization step wherein said polymer for semiconductor lithography is synthesized, in the presence of said purified polymerization initiator that was purified by said filtering step, by a radical polymerization reaction.

2. The method for producing a polymer for semiconductor lithography according to claim 1, wherein said polymerization initiator comprises an azo compound.

3. The method for producing a polymer for semiconductor lithography according to claim 1, wherein said repeating unit (A) comprises at least one structure selected from the group consisting of Formula (A1):

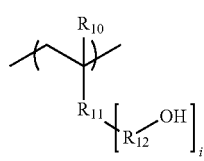

(A1)

wherein $R_{10}$ represents a hydrogen atom, or $C_1$-$C_4$ hydrocarbon group which may be substituted with a fluorine atom(s); $R_{11}$ represents a substituted or unsubstituted aromatic hydrocarbon group; $R_{12}$ represents a single bond, or $C_1$-$C_4$ divalent hydrocarbon group which may be substituted with a fluorine atom(s), or carbonyl; and i represents an integer of 1 or 2;

Formula (A2):

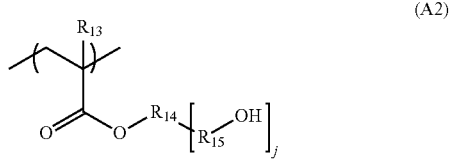

(A2)

wherein $R_{13}$ represents a hydrogen atom, or $C_1$-$C_4$ hydrocarbon group which may be substituted with a fluorine atom(s); $R_{14}$ represents a $C_2$-$C_{14}$ divalent to tetravalent hydrocarbon group which may comprise a fluorine atom, oxygen atom and/or sulfur atom; $R_{15}$ represents a single bond, or $C_1$-$C_4$ divalent hydrocarbon group which may be substituted with a fluorine atom(s), and j represents an integer of 1 to 3; and Formula (A3):

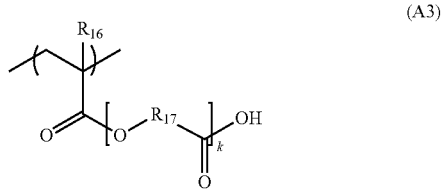

(A3)

wherein $R_{16}$ represents a hydrogen atom, or $C_1$-$C_4$ hydrocarbon group which may be substituted with a fluorine atom(s); $R_{17}$ represents a $C_6$-$C_{12}$ divalent alicyclic hydrocarbon group which may comprise an oxygen atom and/or sulfur atom; and k represents an integer of 0 or 1.

4. The method for producing a polymer for semiconductor lithography according to claim 1, wherein said repeating unit (B) comprises a structure wherein the hydroxy group or carboxy group of said repeating unit (A) is protected with at least one type of acid-dissociable, dissolution inhibiting group selected from the group consisting of Formula (b1):

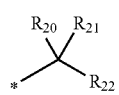

(b1)

wherein * represents the position of linkage of Formula (b1) itself; $R_{20}$ and $R_{21}$ each independently represents a $C_1$-$C_4$ hydrocarbon group; $R_{22}$ represents a $C_1$-$C_{12}$ hydrocarbon group; and $R_{22}$ may be linked to $R_{20}$ or $R_{21}$ to form a ring, and Formula (b2):

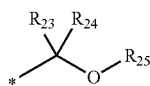

(b2)

wherein * represents the position of linkage of Formula (b2) itself; $R_{23}$ and $R_{24}$ each independently represents a hydrogen atom or $C_1$-$C_4$ hydrocarbon group; $R_{25}$ represents a $C_1$-$C_{12}$ hydrocarbon group; and $R_{23}$ may be linked to $R_{24}$ or $R_{25}$ to form a ring.

5. The method for producing a polymer for semiconductor lithography according to claim 1, wherein said repeating unit (C) comprises a structure represented by Formula (C1):

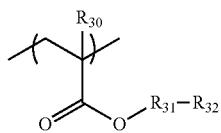

(C1)

wherein $R_{30}$ represents a hydrogen atom, or $C_1$-$C_4$ hydrocarbon group which may be substituted with a fluorine atom(s); $R_{31}$ represents a single bond, $C_1$-$C_4$ alkylene, or a group in which the alkylene is substituted with an oxygen atom(s), carbonyl and/or carbonyloxy; and $R_{32}$ represents a lactone structure-containing group represented by Formula (c):

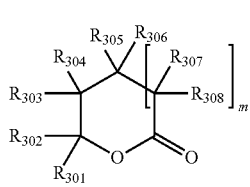

(c)

wherein any one of $R_{301}$ to $R_{308}$ represents a single bond which is the position of linkage of $R_{32}$ itself, and each of the remaining $R_{301}$ to $R_{308}$ represents a hydrogen atom, $C_1$-$C_4$ hydrocarbon group or alkoxy; or any one of $R_{301}$ to $R_{308}$ represents a $C_3$-$C_{14}$ hydrocarbon group that comprises the position of linkage of $R_{32}$ itself and is bound to any one or two of the other $R_{301}$ to $R_{308}$ to form a $C_5$-$C_{15}$ alicyclic ring, which $C_3$-$C_{14}$ hydrocarbon group may comprise an oxygen atom and/or sulfur atom, each of any one or two of the remaining $R_{301}$ to $R_{308}$ represents a single bond for formation of said $C_5$-$C_{15}$ alicyclic ring, and each of the other $R_{301}$ to $R_{308}$ represents a hydrogen atom, $C_1$-$C_4$ hydrocarbon group or alkoxy; and m represents an integer of 0 or 1.

6. The method for producing a polymer for semiconductor lithography according to claim 1, wherein said repeating unit (D) comprises a structure represented by Formula (D1):

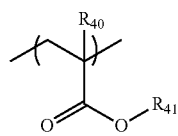

(D1)

wherein $R_{40}$ represents a hydrogen atom, or $C_1$-$C_4$ hydrocarbon group which may be substituted with a fluorine atom(s); $R_{41}$ represents a $C_3$-$C_7$ hydrocarbon group comprising a 3- to 6-membered cyclic ether structure.

7. The method for producing a polymer for semiconductor lithography according to claim 1, wherein said polymerization initiator has not been subjected to washing treatment with water.

8. The method for producing a polymer for semiconductor lithography according to claim 1, wherein said polymerization step uses as a polymerization method a dropping polymerization method.

9. The method for producing a polymer for semiconductor lithography according to claim 1, said method further comprising the step of purification of a polymer obtained by said polymerization step.

10. A method for producing a polymer for semiconductor lithography, said polymer comprising at least one type of repeating units selected from the group consisting of: a repeating unit having a hydroxy group or carboxy group (A), a repeating unit having a structure wherein a hydroxy group or carboxy group is protected with a group that suppresses dissolution into an alkaline developer and is dissociable by the action of an acid (B), a repeating unit having a lactone structure (C), and a repeating unit having a cyclic ether structure (D), said method comprising:

a filtering step, wherein a solution of a polymerization initiator dissolved in an organic solvent is passed through a tilts r having a pore size of not more than 1.0 μm to reduce a sodium content of said polymerization initiator solution to not more than 300 ppb with respect to a weight of said polymerization initiator to produce a purified polymerization initiator; and a polymerization step wherein said polymer for semiconductor lithography is synthesized, in the presence of said purified polymerization initiator, by a radical polymerization reaction, wherein said polymerization step uses a dropping polymerization method using a polymerization reactor comprising at least a storage tank for a solution comprising the polymerization initiator, a polymerization reaction vessel, and said filter placed in a channel connected from said storage tank to said polymerization reaction vessel.

\* \* \* \* \*